United States Patent [19]

Schwebel et al.

[11] 4,124,024

[45] Nov. 7, 1978

[54] DISPOSABLE HYPODERMIC INJECTION AMPULE

[76] Inventors: Paul R. Schwebel, 44045 15th St. West, Lancaster, Calif. 93534; Manuel N. Friend, 311 Bruce Ln., Turlock, Calif. 95380

[21] Appl. No.: 773,970

[22] Filed: Mar. 3, 1977

[51] Int. Cl.$^2$ .............................................. A61M 5/30
[52] U.S. Cl. .......................... 128/173 H; 128/218 NV; 128/218 P
[58] Field of Search ........... 128/173 H, 218 P, 218 F, 128/218 M, 218 A, DIG. 11, 215, 218 NV; 102/92, 37.4, 39, 8; 89/1 B

[56] References Cited

U.S. PATENT DOCUMENTS

| | | | |
|---|---|---|---|
| 2,322,245 | 6/1943 | Lockhart | 128/173 H |
| 2,667,874 | 2/1954 | Dickinson, Jr. | 128/173 H |
| 3,802,430 | 4/1974 | Schwebel et al. | 128/173 H |

*Primary Examiner*—Henry J. Recla
*Attorney, Agent, or Firm*—Robert Louis Finkel

[57] ABSTRACT

A self-contained disposable explosively actuated ampule for performing needleless percutaneous injection. The ampule comprises an outer shell enclosing an elongated inner chamber including a closed rear end containing a propellant charge, a tapered funnel-shaped forward end, and a scored sealing member hermetically sealing the chamber in the area of its funnel shaped end. A metered dose of fluid injectant is confined between the scored sealing member and a sealing plunger separating the injectant from the charge. The plunger is adapted for axial movement within the chamber and comprises a main body having sealing means thereabout which are compressed and tightened against the inner chamber wall, and having a tip portion projecting forwardly from the main body. Gas released at very high pressure by the charge drives the plunger in the chamber and pressurizes the fluid injectant, thereby causing the scored sealing member to rupture and enabling the fluid to be discharged from the chamber forward end. Simultaneously, the outer circumferential surface of the plunger tip sealingly abuts the inner peripheral surface of the chamber forward end. The sealing elements in the plunger main body are comprised of an annular featheredge seal around the rear end of the plunger and annular sealing means about the axial main body of the plunger.

13 Claims, 3 Drawing Figures

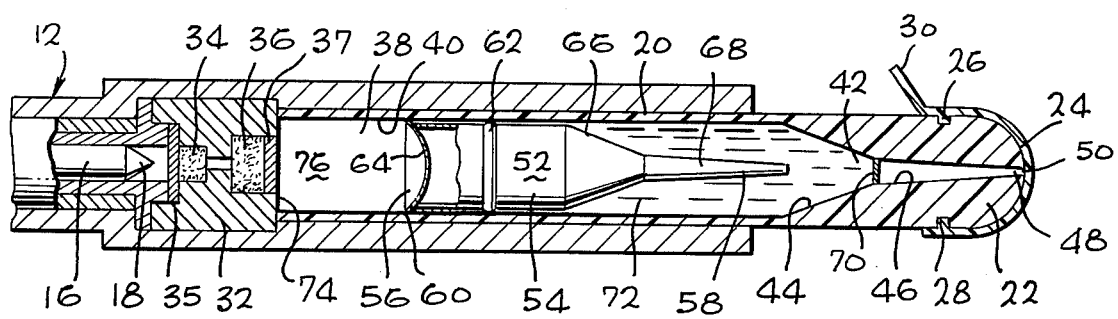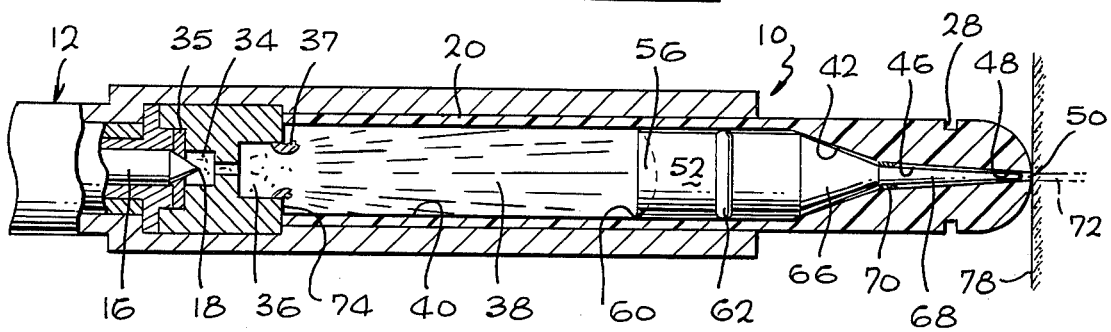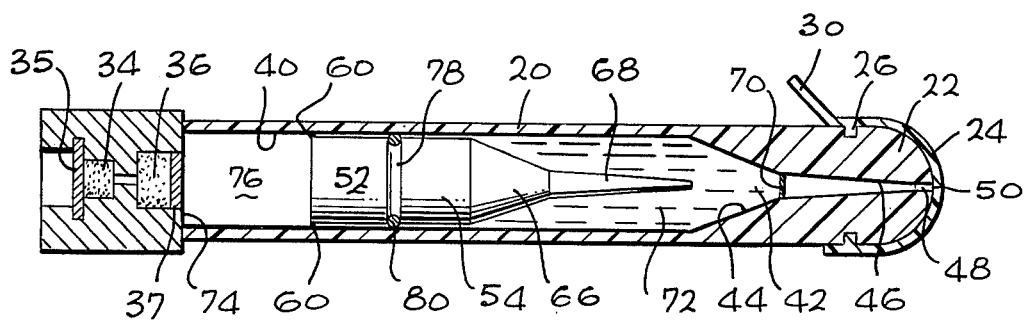

DISPOSABLE HYPODERMIC INJECTION AMPULE

BACKGROUND OF THE INVENTION

1. Field of the Invention

This invention relates to needleless hypodermic medicators for effecting subcutaneous and intramuscular injections of medicaments and the like into animate or inanimate bodies. More specifically, the invention relates to an improved medicator of the type wherein a high pressure, explosive actuated plunger is utilized to discharge a material quantity of injectant fluid from a disposable ampule.

2. Prior Art

Techniques have evolved for subcutaneous innoculations or other injections without the use of a hypodermic needle in which a metered dose of injectant is projected against the skin at such high pressures and velocity that it penetrates the skin. Typically in such apparatus gas is released at very high pressure from a suitable propellant charge, the gas operating a piston or plunger for generating the requisite pressure used to eject the medicament or the like through a fine orifice. The high pressure exerted ejects the medicament in a very fine stream or jet at high velocity, the kinetic energy of which causes the stream to enter the body.

Among this type of prior art devices are those adapted to be fitted with a unitary disposable ampule which contains a quantity of the selected medicament and is provided with a suitable explosive charge at one end, an orifice at its other end and the explosive actuated piston or plunger situated between the charge and the medicament. Under the impulse of combustion of the charge, the piston is forced down the ampule to expel the medicament from the orifice. Detonation of the charge is effected by a discrete reusable actuating unit containing a triggering and firing mechanism. The actuating unit also comprises a housing portion, typically in the form of a barrel, formed to receive the ampule. Such an injection system utilizing a reusable actuated unit for use with a disposable medicant or ampule of the type discussed hereintofore is, for example, disclosed in our co-pending patent application Ser. No. 730,421 filed 7 October 1976 and entitled "PYROTECHNICALLY POWERED NEEDLELESS INJECTOR."

With direct explosive actuation in a closed system where both the medicament and the explosive are loaded in the same capsule or ampule and where the explosively actuated force is generated and applied directly into the piston to expel the medicament from the orifice in the capsule, there has always been the danger of mutual contamination. Prior art attempts to prevent such contamination have not been fully effective, or have been commercially infeasible. To protect the medicament from any gas penetration upon combustion of the propellant charge, it has been proposed in the aforementioned copending application to provide one or a plurality of sealing O-ring members around the piston body. Although the provision of such a sealing arrangement for this type of directly actuated medicator has proved to be satisfactory in most instances, the high peak pressures, pressure surges and rapid pressure fluctuations inherent with this type of injector system, still tend to affect the overall sealing efficiency of the device.

The principal object of the subject invention is to provide a pyrotechnically charged needleless hypodermic injector having novel sealing structure enabling the device to maintain uniform sealing efficiency over a wide range of pressures.

SUMMARY OF THE INVENTION

To achieve its stated objective, and other objects which will become apparent, the subject invention provides a unitary disposable medicator ampule adapted to be fitted in an actuating unit and having loaded within its interior a metered dose of injectant fluid, a gas-producing pyrotechnic propellant charge, and a sealing plunger separating the explosive from the fluid. The latter incorporates novel sealing structure effectively sealing the plunger in the ampule housing and providing positive sealing action to prevent any contamination of the medicament contained in the ampule.

Another object of the invention is to provide a novel ampule for such an injector having an inner chamber enclosing the medicament and incorporating novel sealing structure for hermetically sealing the medicament within the chamber.

Another object is to provide a pyrotechnically operated needleless hypodermic instrument of improved construction with respect to safety, speed and ease of operation.

Still a further object is provision of a simple and improved medicator ampule for performing percutaneous injection painlessly.

Still a further object of the invention is to provide a needleless hypodermic medicator ampule utilizing a pyrotechnically generated force to effect the percutaneous injection of predetermined doses of medication at desired depths with convenience, reliability, and safety.

A further object is to provide a disposable device of such type which can be manufactured economically for mass distribution.

The structure and operation of the subject invention will become apparent to the reader upon consideration of the following detailed description of the preferred embodiments illustrated in the accompanying drawing in which:

THE DRAWING

FIG. 1 is a side sectional view of an ampule embodying the subject invention positioned in the muzzle of a typical injector, prior to discharge;

FIG. 2 is a side sectional view of the ampule and injector of FIG. 1 during detonation and discharge of injectant fluid from the ampule; and FIG. 3 is a side sectional view through another pressure injection ampule embodying the invention.

Whenever possible, like numerals are used to designate the same or equivalent components in the several figures.

DETAILED DESCRIPTION

Referring now to the drawing and with attention initially directed to FIGS. 1 and 3, there is shown a preferred embodiment of the invention comprising a medicator ampule 10, an actuating unit generally referenced by the numeral 12 and including an ampule receiver in the form of an elongated barrel 14 and a firing mechanism in the form of a firing pin 16 having a tip 18.

The actuating unit may be such as disclosed in the aforementioned copending application Ser. No. 730,421.

The ampule 10 consists of an elongated body having an outer shell 20 of polypropylene, polyethylene, acrylic, polycarbonate, nylon, or similar suitable material. The generally dome-shaped forward end 22 of the ampule body is enclosed by a sterile cover 24, e.g., of the styrene type or other suitable material. The cover 24 is held in position on the ampule forward end 22 by means of an inner annular lip 26 retained in an annular groove 28 formed in forward end 22. A tab portion 30 integral with the cover 24 enables the latter to be removed quickly and easily.

The closed rear end of the ampule defines an extended head 32. The head contains an explosive primer or percussion cap 34 operatively connected to a deflagatory charge 36.

A closure 35 and retainer 37 of suitable materials are provided to protect primer 34 and charge 36, respectively.

The outer shell 20 is seen to enclose an inner chamber 38 having a glass liner 40. The forward end 42 of the chamber is tapered. The tapered forward end comprises first and second sections 44, 46, or truncated conical configuration. The extreme forward end of section 46 is configured with an axial aperture 48 terminating in a discharge orifice 50. During storage and transport of the medicator the cover 24 seals the orifice and aperture so as to prevent any contaminant from contacting them or entering the chamber.

Axially slidably disposed within the chamber 38 is a sealing plunger 52. The plunger comprises a main body 54, a rear end 56, and a tapered forward end or tip 58. The main body has an outer diameter chosen to correspond closely to the inner diameter of chamber 38 so as to provide a snug fit with the chamber's wall 40. Positive frictional and sealing contact between the plunger main body 54 and the chamber wall defined by the glass liner 40 is effected by sealing means 60 and 62. The sealing means 60 are in the form of an annular featheredge seal formed by the edge or rim defined by a concavity in the main body, e.g., a hemispherical recess 64 formed in the rear end 56 of the plunger main body 54. The sealing means 62 in the embodiment shown in FIG. 1 is in the form of a molded seal which sealingly abuts the wall of liner 40.

The tapered forward end or tip 58 comprises first and second sections 66, 68 shaped as conical frustums and closely co-responding to the inner peripheral sections 44, 46 of the chamber tapered forward end 42.

An additional sealing member in the form of a scored membrane 70, typically of silicone rubber, is provided to hermetically seal the chamber 38. As shown, the membrane 70 is located at the intersecting points of the conical walls of the sections 44 and 46.

A metered quantity of fluid injectant 72 is loaded and confined between the plunger forward tapered end and the membrane 70. Frictional contact between the plunger sealing members 60, 62 and the inner wall of the chamber's liner 40, on the one hand, and the fixedly secured membrane 70, on the other hand, thus prevent premature discharge of the injectant charge 72 from the ampule. Also, since the plunger and membrane are immobile prior to use, the charge 70 is in a state of pressure equilibrium within the ampule during storage and transport.

The region of bore 38 between the rear end 56 of the plunger and the forward end 74 of the ampule extended head 32 may be considered the pressure chamber 76 of the instrument.

In operation as shown in FIG. 2, the actuating unit 12 is activated by a triggering device, not shown, which releases the firing pin 16 with a force sufficiently high to drive its tip 18 through the closure 35 and into the primer 34, thereby detonating charge 36. The gases generated by the slow burning charge burst through retainer 37, fill and build up pressure within chamber 76, and drive plunger 52 into the tapered end 42 of the chamber. Under the thrust of plunger 52 the fluid charge 72 ruptures the scored membrane 70 and fills the foremost sections 46 and 48 of the chamber. As the fluid pressure rapidly increases, the medicament 72 is discharged from orifice 50 in a high-velocity stream with sufficient force to penetrate the skin 78.

The sustaining force of the expending combustion products drives the plunger 52 toward the end of its stroke, at which point the surfaces of sections 66, 68 of its tip 58 are in sealing engagement with the abutting inner surfaces of sections 44, 46 of the chamber forward end 42.

As shown in FIG. 2, an additional seal is provided between the plunger tip 58 and the chamber wall in the region 46 by the membrane 70, which as a result of penetration of the tip 58 is expanded forwardly into the region 46 of the chamber and compressed tightly between the abutting surfaces of the plunger tip and the chamber forward end.

It should be noted that under the impulse of combustion of the charge 36, the edge 60 of concavity or recess 64 is flared radially outwardly into tight sealing engagement with the chamber liner 40 in region 46 due to the extremely high explosively generated force exerted directly on the plunger rearward end 56. Such a sealing arrangement, per se, prevents the penetration of hot gases past the featheredge seal 60. Should this seal 60 fail and permit a minimal amount of gases in some manner to pass, such gases would be intercepted and restrained by the molded seal 62.

The sealing structure of the arrangement illustrated in FIG. 3 is substantially identical with that of FIGS. 1 and 2, except that the plunger does not employ molded sealing means 62. Instead, an annular frame or recess 78 is provided in the circumference of main body 54 of the plunger and an O-ring 80 is seated in the recess 78.

It will be appreciated that instead of a single molded seal member 62 as shown in FIG. 1 and 2, or a single O-ring seal as illustrated in FIG. 3, a plurality of such sealing means may be utilized and may, for example, be arranged about the plunger main body in parallel relation to each other.

By selectively varying the quantity, and other characteristics of propellant charge 36, the resiliency and frictional properties of the plunger 52 and sealing means 60, 62 and 80, the dimensions of the chamber 38 and ampule 10, and the size and design of orifice 50, the dosage, depth of penetration through the skin and various other injection parameters can readily be established at the time of manufacture.

With the medicator ampule described above, improved injector pressure-time characteristics are obtained because of the closed ballistic system provided between the propellant charge 36 and plunger 52. The initial pressure acting against the plunger is extremely high and thereafter falls gradually to an injection-sustaining pressure level adequate to discharge all of the ampule contents. The heat insulating liner 40 of glass material serves to sustain the injection-producing pressure level. Some evidence suggests that in the absence of such a liner, the terminal pressure would fall or chop too rapidly, causing fluctuations or pressure surges, which some patients experience as pain.

During manufacture of the medicator ampule described, the glass lining 40 is initially formed, in conventional manner, with an open rear end and an open ended conical frustum at its forward end. Subsequently the plunger 52 is loaded into the glass liner or housing and held at the desired depth. Then, the space forward of the plunger is filled with a metered dose of medicament or the like, and the scored membrane 70 is sealed over and across the open forward end of the glass liner. Thereafter, the outer shell 20, which is molded to conform closely to the glass liner, is slipped around the liner while hot from the mold. Shrinkage of the plastic shell on cooling insures tight fit. Finally, the sterile cover is placed in position over forward end 22.

Although the foregoing description relates to what are believed to be preferred embodiments, it is to be understood that those skilled in the art may make changes and modifications without departing from the spirit and scope of the invention as set forth in the appended claims.

We claim:

1. In a needleless hypodermic injector operable by propellant gas generated from the detonation of an explosive charge, a disposable ampule comprising:
    an elongated casing having an axial bore therein, said bore including an inwardly tapered portion at one end of said casing terminating in a fine orifice through said casing;
    a cavity in said casing containing a propellant charge and in communication with said bore at the opposite end of said casing;
    a gas-operated piston slidably and sealingly mounted in said bore for sliding axial movement therein in the direction of said orifice upon detonation of said charge, said piston having a tip portion conforming closely to the inwardly tapered portion of said bore;
    a rupturable sealing member positioned in said tapered portion of said bore nearer said orifice, and with said piston defining a chamber in said bore for a measured dose of injectant fluid, said sealing member including means adapted to rupture under pressure exerted by said fluid in response to axial movement of said piston upon detonation of said charge, and to retrovert and deform into an hermetic seal between the tip portion of said piston and the inwardly tapered portion of said bore.

2. The disposable ampule of claim 1, comprising sealing means on said piston providing an hermetic seal between said piston and the inner wall of said bore for preventing leakage of combustion products into said fluid containing chamber following detonation of said charge.

3. The disposable ampule of claim 2, wherein said piston comprises a main body having an outer wall conforming closely with the inner wall of said bore and having a shallow recess formed in the end thereof remote from said orifice, said recess having a rim defining a feather-edge seal between said piston and the inner wall of said bore.

4. The disposable ampule of claim 3, wherein said rim is adapted to be flared outwardly into sealing engagement with the inner wall of said bore by the high impulse of the propellant gas generated from the detonation of said charge.

5. The disposable ampule of claim 3, wherein the main body of said piston is provided with at least one O-ring sealing member.

6. The disposable ampule of claim 3, wherein the main body of said piston comprises at least one integrally formed peripheral seal conforming closely with the inner wall of said bore.

7. The disposable ampule of claim 1, wherein said inwardly tapered portion of said bore comprises a first inwardly tapered section adjacent said orifice, and a second inwardly tapered section in communication with said first section, extending outwardly of said first section.

8. The disposable ampule of claim 7, wherein said sealing member is positioned between said first and second inwardly tapered sections.

9. The disposable ampule of claim 1, wherein said inwardly tapered portion of said bore comprises a first truncated conical section adjacent said orifice, and a second truncated conical section in communication with said first section, extending outwardly of said first section.

10. The disposable ampule of claim 1, wherein said sealing member comprises rupturable scored membrane.

11. The disposable ampule of claim 1, wherein said sealing member is positioned in the inwardly tapered portion of said bore.

12. The disposable ampule of claim 1, wherein said casing comprises a hollow outer cylindrical shell of thermoplastic material, having a snugly fitting heat insulating glass liner defining the inner wall of said bore.

13. The disposable ampule of claim 1, comprising a measure dose of injectant fluid.

* * * * *